United States Patent [19]

Krutak et al.

[11] Patent Number: 5,442,086

[45] Date of Patent: Aug. 15, 1995

[54] ULTRAVIOLET LIGHT-ABSORBING COMPOUNDS AND SUNSCREEN FORMULATIONS AND POLYMERIC MATERIALS CONTAINING SUCH COMPOUNDS OR RESIDUES THEREOF

[75] Inventors: James J. Krutak; Max A. Weaver; Clarence A. Coates, Jr., all of Kingsport; Samuel D. Hilbert, Jonesborough; Terry A. Oldfield, Kingsport; William W. Parham, Kingsport; Wayne P. Pruett, Kingsport, all of Tenn.

[73] Assignee: Eastman Chemical Company, Kingsport, Tenn.

[21] Appl. No.: 308,863

[22] Filed: Sep. 19, 1994

Related U.S. Application Data

[60] Division of Ser. No. 994,069, Dec. 18, 1992, Pat. No. 5,374,419, which is a continuation of Ser. No. 733,769, Jul. 22, 1991, abandoned, which is a division of Ser. No. 395,386, Aug. 17, 1989, Pat. No. 5,057,594.

[51] Int. Cl.$^6$ .................................................. C07C 255/00
[52] U.S. Cl. .................................. 558/401; 558/402; 548/473; 548/476; 548/477; 548/545; 548/546; 424/59; 424/60
[58] Field of Search ............... 558/401, 402; 548/473, 548/476, 477, 545, 546; 424/59, 60

[56] References Cited

U.S. PATENT DOCUMENTS

| | | | |
|---|---|---|---|
| 3,706,700 | 12/1972 | Kirchmayr et al. | 106/178 |
| 4,041,063 | 8/1977 | Buck | 556/98 |
| 4,617,374 | 10/1986 | Pruett et al. | 528/288 |
| 4,707,537 | 11/1987 | Pruett et al. | 528/288 |
| 4,749,773 | 6/1988 | Weaver et al. | 528/288 |
| 4,749,774 | 6/1988 | Weaver et al. | 528/288 |
| 5,302,740 | 4/1994 | Krutak et al. | 558/401 |

*Primary Examiner*—Samuel A. Acquah
*Attorney, Agent, or Firm*—Bernard J. Graves, Jr.; Harry J. Gwinnell

[57] ABSTRACT

Disclosed are certain poly-methine compounds having the formula

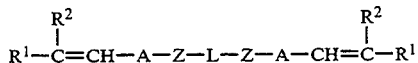

wherein each $R^1$ is independently selected from cyano; carboxy; alkenyloxycarbonyl; an unsubstituted or substituted alkoxycarbonyl, cycloalkoxycarbonyl or aryloxycarbonyl radical; an unsubstituted or substituted, carbocyclic or heterocyclic aryl radical; an unsubstituted or substituted alkanoyl, cycloalkanoyl or aroyl radical; an unsubstituted or substituted carbamoyl radical; or an unsubstituted or substituted alkylsulfonyl, cycloalkylsulfonyl or arylsulfonyl radical; each $R^2$ is independently selected from cyano or an unsubstituted or substituted alkoxycarbonyl, cycloalkoxycarbonyl or aryloxycarbonyl radical; each A is independently selected from an unsubstituted or substituted 1,2-phenylene or 1,2-naphthylene radical; each Z is independently selected from —O— or —S—; and L is an organic linking group bonded by non-oxo carbon atoms to each Z atom. Also disclosed are sunscreen formulations and polymeric compositions containing at least one of the poly-methine compounds or the reactive residue thereof.

2 Claims, No Drawings

ULTRAVIOLET LIGHT-ABSORBING COMPOUNDS AND SUNSCREEN FORMULATIONS AND POLYMERIC MATERIALS CONTAINING SUCH COMPOUNDS OR RESIDUES THEREOF

This is a divisional application of application Ser. No. 07/994,069 filed on Dec. 18, 1992, which is now U.S. Pat. No. 5,374,419, File Wrapper Continuation of application Ser. No. 07/733,769 filed Jul. 22, 1991, (abandoned), which is a Division of application Ser. No. 07/395,386 filed Aug. 17, 1989, (U.S. Pat. No. 5,057,594, issued Oct. 15, 1991).

This invention pertains to certain novel poly-methine compounds which exhibit unique ultraviolet light absorbing properties. This invention also concerns polymer compositions containing at least one of the poly-methine compounds which are useful for protecting various substrates from the deleterious effects of ultraviolet light.

Recently, considerable attention has been given to the observed increase in skin cancer attributed in part to people's lifestyles and leisure activities that result in excessive and prolonged exposure to harmful ultraviolet (UV) light rays present in solar radiation. The UV rays have been divided into three regions: UV-A Region (320–400 nm), UV-B Region (290–320 nm) and UV-C Region (200–290 nm). The UV-C Region has the highest energy and most damaging radiation, but is largely absorbed by the ozone layer. UV light in the UV-B Region, also called the Erythemal or Burning Region, causes sunburn and is responsible for most of the immediate damage to the human body, i.e., skin and hair. UV-A radiation, also called the Tanning Region, causes tanning but also may cause reddening of the skin and sunburn upon prolonged exposure.

Traditionally, sunscreen formulations have contained UV light-absorbing chemicals capable of absorbing most of the UV-B light, which is the most likely to cause severe sunburn. Recently, to achieve a greater degree of protection, formulations have included a combination of UV-A and UV-B light absorbing compounds. See, for example, N. A. Shaath, Cosmetics and Toiletries, 101, March 1986, PP 55–70 and Consumer Reports, June 1988, pp 370–374. These formulations have been designed to absorb most of the UV light in the range of 280 to 400 nm, particularly in the 280 to 360 nm range which contains the most damaging UV light.

The novel poly-methine compounds provided by this invention absorb UV light over a wide range of wavelengths, e.g., 280 to 400 nm, which renders them suitable for use in formulating various products that provide protection from the damaging rays present in sunlight and, also, in fluorescent light. The polymethine compounds of our invention have the formula

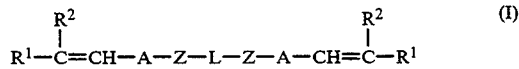

wherein
each $R^1$ is independently selected from cyano; carboxy; alkenyloxycarbonyl; an unsubstituted or substituted alkoxycarbonyl, cycloalkoxycarbonyl or aryloxycarbonyl radical; an unsubstituted or substituted, carbocyclic or heterocyclic aryl radical; an unsubstituted or substituted alkanoyl, cycloalkanoyl or aroyl radical; an unsubstituted or substituted carbamoyl radical; or an unsubstituted or substituted alkylsulfonyl, cycloalkylsulfonyl or arylsulfonyl radical;

each $R^2$ is independently selected from cyano or an unsubstituted or substituted alkoxycarbonyl, cycloalkoxycarbonyl or aryloxycarbonyl radical;

each A is independently selected from an unsubstituted or substituted 1,2-phenylene or 1,2-naphthylene radical;

each Z is independently selected from —O— or —S—; and

L is an organic linking group bonded by non-oxo carbon atoms to each Z atom.

The described poly-methine compounds have been found to exhibit two strong absorption bands of almost equal intensity, a characteristic which renders the compounds particularly effective in absorbing UV light over an extended wavelength range. This absorption renders the compounds unique since prior art compounds derived from p-hydroxybenzaldehyde and various active methylene compounds such as cyanoacetic acid esters, for example those disclosed in U.S. Pat. Nos. 3,706,700, 4,617,374, 4,707,537, 4,749,773 and 4,749,774, exhibit only one major absorption band, which results in their absorbing UV light over a limited range. Cinnamic acid derivatives, such as alkyl p-alkoxycinnamates, are known to be useful UV-B absorbers, having an absorption maximum in the 300 to 310 range, for sunscreen preparations.

The two major absorption bands exhibited by our novel compounds are particularly advantageous since those bands correspond roughly to the UV-A and UV-B regions of the UV spectrum. This allows formulation of sunscreen preparations which absorb most of the UV light over the range of 290 to 400 nm using only one active LrV light-absorbing ingredient. Since currently available sunscreen products may cause skin sensitization and allergic reactions, a particularly valuable embodiment of our invention includes polymeric compositions, e.g., polyesters, having reacted therewith or copolymerized therein at least one compound of formula (I) which contains one or more reactive groups. These polymeric compositions are not readily absorbed through the stratum corneum layer of the skin and thus contact of the UV light-absorbing agent with the epidermis is prevented or reduced substantially.

The polymer compositions provided by this invention comprise a condensation polymer such as ester-containing polymers, including polycarbonates and, especially, polyesters, (1) having physically admixed therein one or more of the poly-methine compounds of formula (I) and (2) having reacted therewith or copolymerized therein the residue of at least one of the compounds of formula (I). Certain of the polymer compositions may be used, as mentioned above, as UV light absorbers in sunscreen preparations. The polymer compositions also may be used in the preparation of coatings, film and sheet material for protecting substrates from UV light. For example, sheet material fabricated from the polymer compositions of our invention may be used in the manufacture of articles designed to protect the eyes from excessive exposure to UV radiation.

The polymer compositions of this invention also may be used in the manufacture of containers suitable for packaging a variety of materials. Many products such as certain fruit juices, condiments, beverages, food products, cosmetics and shampoos are affected deleteriously, i.e., degraded, by UV radiation from natural sunlight or from artificial sources such as fluorescent lighting. In most cases these photochemical reactions are dependent on the wavelength of the radiation and generally increase significantly with radiation of decreasing wavelength. UV radiation in the range of 290 to 380 nm is the most damaging. Thus, as the absorption by the packaging material of this portion of the spectrum increases, the less the degradation of UV-sensitive products contained therein will be. The compounds of formula (I) or residues thereof advantageously absorb a substantial portion of such damaging UV radiation, even when used in low concentrations, and are stable under the conditions, e.g., the high temperatures, at which the condensation polymers are manufactured and/or processed.

With reference to formula (I), the alkyl and alkoxy moieties of the groups recited in the definitions of $R^1$ and $R^2$ can be unsubstituted or substituted alkyl and alkoxy of up to about 24 carbon atoms. Hydroxy, alkoxy, hydroxyalkoxy, halogen, alkanoyloxy, alkoxycarbonyl, cyano, carbamoyl, aryl, aryloxy, cycloalkyl, cycloalkoxy, alkylthio, arylthio, hydroxyalkylthio, alkanoylamino, aroylamino, alkylsulfonamido, arylsulfonamido, succinimido, phthalimido and the heterocyclic groups set forth below are examples of the substituents which may be present on the substituted alkyl groups and alkoxy moieties which $R^1$ and $R^2$ can represent. The cycloalkyl moieties of the groups recited in the definitions of $R^1$ and $R^2$ can be unsubstituted cycloalkyl of 5 to 7 carbon atoms which may be substituted with alkyl or any of the substituents mentioned hereinabove. The carbamoyl groups which $R^1$ can represent may be unsubstituted or substituted carbamoyl such as N-alkylcarbamoyl, N,N-dialkylcarbamoyl, N-cycoalkylcarbamoyl, N-alkyl-N-cycloalkylcarbamoyl, N-arylcarbamoyl, N-alkyl-N-arylcarbamoyl and the like.

The aryl moieties of the groups recited in the definitions of $R^1$ and $R^2$ can be unsubstituted or substituted carbocyclic aryl containing 6 to about 12 carbon atoms or unsubstituted or substituted heterocyclic aryl containing 5 to about 10 ring atoms. Examples of the substituents which may be present on the aryl groups include alkyl and the substituents set forth in the preceding paragraph. Pyrrolyl, pyridyl, pyrimidyl, 2-benzothiazolyl, 2-benzoxazolyl, 2-benzimidazolyl, 2-thienyl, 2-furanyl, 1,3,4-thiadiazol-2-yl, 1,2,4-thiadiazol-5-yl and groups having the structure:

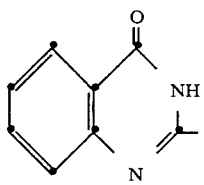

are examples of the unsubstituted aromatic heterocyclic residues which each $R^2$ may represent.

The 1,2-phenylene and 1,2-naphthylene residues represented by A can be unsubstituted or substituted, for example, with alkyl, cycloalkyl, aryl, alkoxy, halogen, etc. Further descriptions and examples of the methine residues

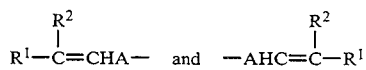

of the poly-methine compounds of formula (I) are set forth in U.S. Pat. Nos. 4,338,247, 4,340,718, 4,617,374 and 4,661,566, the disclosures of which are incorporated herein by reference. Phenylene and methylene residues A are bonded to the methine residues at the 1-position and to oxygen or sulfur atoms Z at the 2-position.

The organic linking group represented by L is bonded to the adjacent oxygen or sulfur atoms (atoms represented by Z) through non-oxo carbon atoms, i.e., atoms Z are bonded directly to non-carbonylic carbon atoms, e.g., unsubstituted or substituted methylene groups, a methylidene group and an unsubstituted methylene group or a nuclear carbon atom of a carbocyclic or heterocyclic aromatic group. Thus, linking group L is selected from a wide variety of alkylene, alkenylene, alkynylene, cycloalkylene, carbocyclic and heterocyclic arylene and combinations of such divalent groups. The alkylene linking groups may contain within their main chain hetero atoms, e.g., oxygen, sulfur, sulfonyl, nitrogen, substituted nitrogen, and/or cyclic groups such as cycloalkylene, carbocyclic arylene, divalent aromatic heterocyclic groups or ester moieties such as

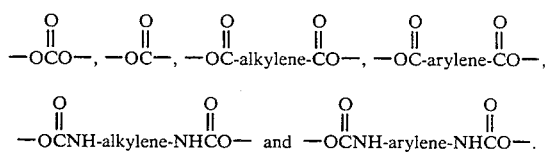

Examples of alkylene linking groups containing a cyclic moiety in the linking chain include:

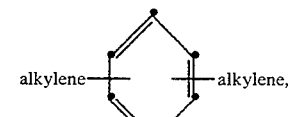

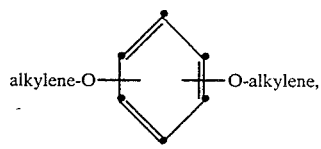

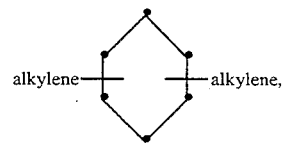

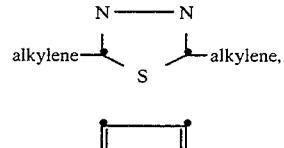

-continued

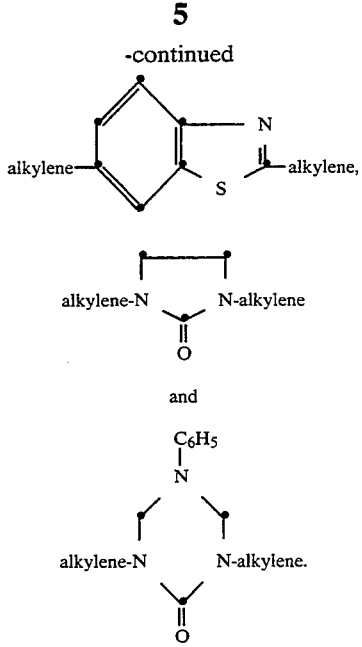

alkylene—⟨benzothiazole⟩—alkylene, alkylene-N    N-alkylene
        \\  //
         C
         ‖
         O and

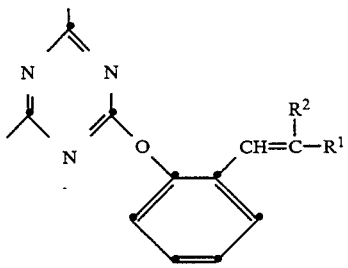

The carbocyclic groups may be cycloalkylene such as 1,2-, 1,3- and 1,4-cyclohexylene, 1,2-, 1,3- and 1,4- phenylene and 2,6- and 2,7-naphthylene. Examples of the divalent heterocyclic groups include unsubstituted and substituted triazines such as 1,3,5-triazin-2,4-diyl, 6-methoxy-1,3,5-triazin-2,4-diyl and the group having the structure:

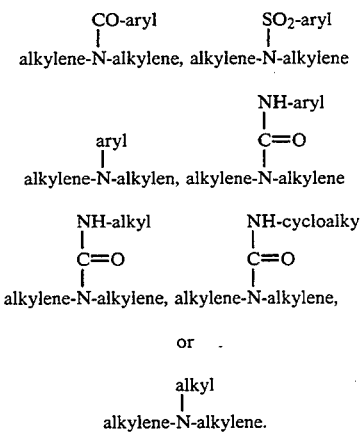

wherein $R^1$ and $R^2$ are defined hereinabove; diazines such as 2,4-pyrimidindiyl, 6-methyl-2,4-pyrimidindiyl, 6-phenyl-2,4-pyrimidindiyl, 3,6-pyridazindiyl and 2-methyl-3-oxo-4,5-pyridazindiyl; dicyanopyridines such as 3,5-dicyano-2,6-pyridindiyl and 4-phenyl-3,5-cyano-2,6-pyridindiyl; quinolines and isoquinolines such as 2,4-quinolindiyl and 2,8-isoquinolinediyl; quinoxalines such as 2,3-quinoxalindiyl; and azoles such as 2,5-thiazoldiyl, 5-methylene-2-thiazolyl, 3,5-isothiazoldiyl, 5-methylene-3-isothiazolyl, 1,3,4-thiadiazol-2,5-diyl, 1,2,4-thiadiazol-3,5-diyl, 2,6-benzothiazoldiyl, 2,5-benzoxazoldiyl, 2,6-benzimidazoldiyl, 6-methylene-2-benzothiazolyl and the group having the structure:

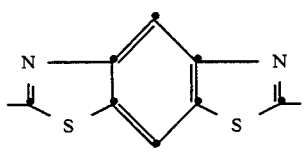

and maleimides such as 1-methyl-3,4-maleimidediyl and 1-phenyl-3,4-maleimidediyl. The acyclic moieties of the linking group represented by L also may be substituted, for example, with hydroxy, alkoxy, halogen, alkanoyloxy, cyano, alkoxycarbonyl, aryl, aryloxy, cycloalkyl, etc. The cyclic moieties of linking group L may be substituted with alkyl as well as with the substituents already mentioned. In addition to the possible substitution described above, the nitrogen atom of the nitrogen containing alkylene groups may be substituted, for example, with alkyl, aryl, alkanoyl, aroyl, alkylsulfonyl, or carbamoyl, e.g., $$\begin{array}{cc} \text{CO-aryl} & \text{SO}_2\text{-aryl} \\ | & | \\ \text{alkylene-N-alkylene,} & \text{alkylene-N-alkylene} \end{array}$$

$$\begin{array}{cc} & \text{NH-aryl} \\ \text{aryl} & | \\ | & \text{C}=\text{O} \\ \text{alkylene-N-alkylen,} & | \\ & \text{alkylene-N-alkylene} \end{array}$$

$$\begin{array}{cc} \text{NH-alkyl} & \text{NH-cycloalkyl} \\ | & | \\ \text{C}=\text{O} & \text{C}=\text{O} \\ | & | \\ \text{alkylene-N-alkylene,} & \text{alkylene-N-alkylene,} \end{array}$$

or $$\begin{array}{c} \text{alkyl} \\ | \\ \text{alkylene-N-alkylene.} \end{array}$$

The poly-methine compounds which may be reacted with or copolymerized in a condensation polymer to obtain one embodiment of our novel polymer compositions must bear or contain at least one substituent that is reactive with one of the monomers from which the condensation polymer is derived. Examples of such reactive substituents include carbonyl halides such as carbonyl chloride, carboxy, alkoxycarbonyl, alkenyloxycarbonyl, cycloalkoxycarbonyl, aryloxycarbonyl, amino, hydroxy, esterified hydroxy, i.e., acyloxy, groups such as carboxylic acid esters, e.g., alkanoyloxy, cycloalkanoyloxy and aroyloxy, carbamic acid esters, e.g., N-alkylcarbamoyloxy and N-arylcarbamoyloxy and carbonate esters, e.g., ethoxycarbonyloxy. The poly-methine residue may be incorporated into or on the polymer chain by reacting one or more poly-methine compounds of formula (I) with the monomers, with a prepolymer or with the final polymer. As those skilled in the art will appreciate, when the reactive substituent or substituents are alkoxycarbonyl, alkenyloxycarbonyl, cycloalkoxycarbonyl, aryloxycarbonyl, or acyloxy, the alkyl, alkenyl, cycloalkyl and aryl residues and the acid residues of the acyloxy substituents are displaced or removed from the poly-methine compound upon reaction with the polymer or polymer precursor.

The preferred poly-methine compounds of our invention are those wherein $R^1$ is an unsubstituted or substituted alkoxycarbonyl, cycloalkoxycarbonyl or aryloxycarbonyl radical containing up to about 20 carbon atoms;

$R^2$ is cyano;

A is unsubstituted 1,2-phenylene;

Z is —O—; and

L is alkylene of up to 12 carbon atoms, 2-hydroxy-1,3-propanediyl, 2-methyl-1,3-propanediyl, oxy-bis-ethylene, i.e., —CH$_2$CH$_2$OCH$_2$CH$_2$—, oxy-bis-1,4-butanediyl, sulfonyl-bis-ethylene, thio-bis-ethylene, 1,2-, 1,3- and 1,4-phenylene-bis-methylene, 1,2-, 1,3- and 1,4-phenylene-bis-ethylene, 1,4- cyclohexylene-bis-methylene, 1,2-, 1,3- and 1,4-phenylene-bis-(oxyethylene), i.e., —CH₂CH₂O—C₆H₄—O—C₆H₄—OCH₂CH₂—, methylsulfonylimino-bis-ethylene, phenylimino-bis-ethylene, acetylimino-bis-ethylene, phenylcarbamoylimino-bis-ethylene and 1,2-, 1,3- and 1,4-phenylene. The poly-methine compounds which are particularly preferred have the formula

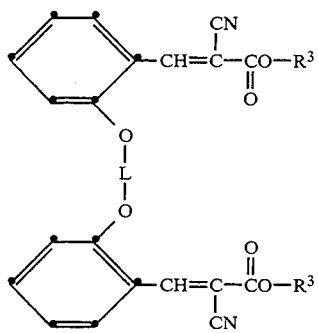

wherein $R^3$ is alkyl of up to about 20 carbon atoms and L is alkylene of 2 to 8 carbon atoms, 1,2-, 1,3- or 1,4-phenylenedimethylene or 1,2-, 1,3- or 1,4-phenylenediethylene.

The poly-methine compounds provided by this invention may be prepared according to known procedures by reacting aldehydes (III) with active methylene compounds (IV) under Knoevenagel conditions:

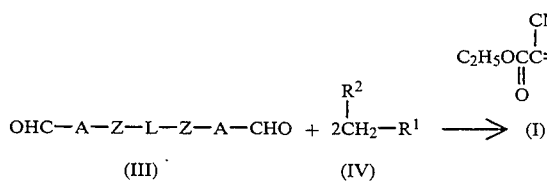

Aldehydes (III) may be obtained by reacting arylaldehydes (V) with dialkylating agents (VI) using published procedures for the preparation of ethers:

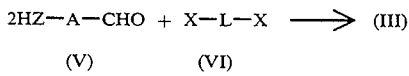

wherein A, Z and L are defined hereinabove and X is halogen, especially chloro or bromo, or an organic sulfonate group, especially methylsulfonyloxy. In general, the dialkylating compounds (VI) may be prepared by reacting the corresponding diol, HO-L-OH, with a hydrohalic acid or an organic sulfonyl halide such as methylsulfonyl chloride, benzenesulfonyl bromide and toluenesulfonyl chloride.

The preparation of the poly-methine compounds is further illustrated by the following examples.

EXAMPLE 1

Salicylaldehyde (29.7 g, 0.243 mol), 1,2-dibromoethane (22.9 g, 0.122 mol), water (200 mL) and 50 percent aqueous sodium hydroxide (19.5 g, 0.244 mol) are mixed and heated with stirring at 90° to 95° C. under nitrogen for about 24 hours. The reaction mixture is then cooled and the pH is adjusted to 9. The product is collected by filtration, washed with water and then isopropanol and dried in air to yield crude 2,2'-[(1,2-ethanediyl)bis(oxy)]bis[benzaldehyde]. The crude product is mixed with isopropanol and the mixture is heated for 20 minutes and then cooled. The product is again collected by filtration, washed with isopropanol and air dried to give 16.2 g of product. A 12.5 g portion of the product is purified further by heating to boiling in methanol (250 mL) and then filtered hot to remove a small amount of a black residue. Upon cooling the filtrate, the product precipitates and is collected by filtration and air dried to yield 6.37 g of purified product having a melting point of 126°-128° C. The identity of the compound thus produced is confirmed by mass spectrometry analysis.

A mixture of 2,2'-[(1,2-ethanediyl)bis(oxy)]bis[benzaldehyde] (2.70 g, 0.01 mol), methyl cyanoacetate (2.0 g, 0.02 mol), methanol (25 mL) and piperidine acetate (70 mg) is heated at reflux for about 2 hours and then cooled. The solid material thus formed is collected by filtration, washed with methanol and dried in air. A yield of 3.95 g, 91.4% of theory, of dimethyl 3,3'-[(1,2-ethanediyl)bis(oxy)]bis[2,1-(phenylene)]bis[2-cyano-2-propenoate] melting at 194°-196° C. is obtained. Mass spectroscopy confirms the structure of the product which exhibits absorption maxima at 296 nm ($\epsilon$=23,400) and 349 nm ($\epsilon$=19,232) in methylene chloride.

The analogous 1,4-isomer having the structure

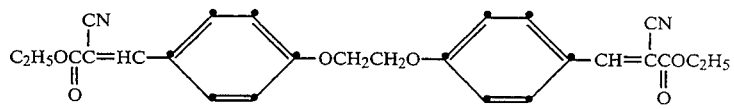

exhibits a single absorption maximum at 343 nm in methylene chloride.

EXAMPLE 2

A mixture of 2,2'-[(1,2-ethanediyl bis (oxy)]-bis [benzaldehyde] (2.70 g, 0.01 mol), methylsulfonyl-acetonitrile (2.38 g, 0.02 mol), methanol (30 mL) and piperidine acetate (50 mg) is heated with stirring at reflux for 2 hours. The reaction mixture is then cooled and the product is collected by filtration, washed with methanol and air dried. A yield of 4.07 g (86.2% of theory) of 3,3'-[(1,2-ethanediyl)-bis(oxy) 2,1-(phenylene)]bis[2-(methylsulfonyl)-2-propenenitrile] melting at 235°-238° C. is obtained. This poly-methine compound exhibits absorption maxima at 296 nm ($\epsilon$=23,935) and at 349 ($\epsilon$=16,992) in methylene chloride.

The analogous 1,4-isomer having the structure

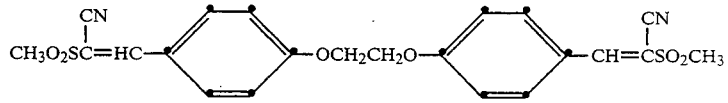

exhibits a single absorption maximum at 340 nm in methylene chloride.

Additional examples of the poly-methine compounds provided by this invention are set forth in Tables I and II. The compounds may be prepared according to the procedures described above and conform to formulas given for each table.

TABLE I

[Structure: Two substituted benzene rings connected by N-L-N linkage, each bearing CH=C(R²)(R¹) substituent with R⁴ on the ring]

| Example | R¹ | R² | R⁴ | Z | L |
|---|---|---|---|---|---|
| 3 | —COOC$_2$H$_5$ | —CN | H | O | —CH$_2$CH$_2$— |
| 4 | —COOCH$_2$CH(C$_2$H$_5$)(CH$_2$)$_4$H | —CN | H | O | —CH$_2$CH$_2$— |
| 5 | —COO(CH$_2$)$_4$H | —CN | H | O | —(CH$_2$)$_4$— |
| 6 | —COO(CH$_2$)$_8$H | —CN | H | O | —CH$_2$CH$_2$OCH$_2$CH$_2$— |
| 7 | —COO(CH$_2$)$_{10}$H | —CN | H | O | —CH$_2$CH$_2$SCH$_2$CH$_2$— |
| 8 | —COO(CH$_2$)$_8$H | —CN | H | O | —CH$_2$CH$_2$SO$_2$CH$_2$CH$_2$— |
| 9 | —COOC$_6$H$_8$-3,3,5-tri-CH$_3$ | —CN | H | O | —CH$_2$CH$_2$N(SO$_2$CH$_3$)CH$_2$CH$_2$— |
| 10 | —COOC$_6$H$_9$-2-CH(CH$_3$)$_2$-5-CH$_3$ | —CN | H | O | —CH$_2$C$_6$H$_4$-4-CH$_2$— |
| 11 | —COO(CH$_2$)$_{12}$H | —CN | H | O | —CH$_2$CH$_2$OC$_6$H$_4$-4-OCH$_2$CH$_2$— |
| 12 | —COOCH$_2$CH=CH$_2$ | —CN | H | O | —CH$_2$CH$_2$N(C$_6$H$_5$)CH$_2$CH$_2$— |
| 13 | —COOCH$_2$C(CH$_3$)=CH$_2$ | —CN | H | O | —(CH$_2$)$_4$O(CH$_2$)$_4$— |
| 14 | —COOCH$_2$CH$_2$O(CH$_2$)$_{10}$H | —CN | H | O | -1,4-C$_6$H$_4$— |
| 15 | —COO(CH$_2$)$_{10}$OH | —CN | H | O | -1,4-C$_6$H$_{10}$— |
| 16 | —COOCH$_2$CH$_2$O(CH$_2$)$_4$H | —CN | H | O | —CH$_2$CH(OH)CH$_2$— |
| 17 | —COO(CH$_2$)$_4$OOCCH$_3$ | —CN | H | O | —CH$_2$CH$_2$CH(OH)CH$_2$— |
| 18 | —COO(CH$_2$)$_{12}$OOCCH$_3$ | —CN | H | O | —CH$_2$CH[OOC(CH$_2$)$_4$H]CH$_2$— |
| 19 | —COOCH$_2$C$_6$H$_5$ | —CN | H | O | —CH$_2$CH(OCOOC$_2$H$_5$)CH$_2$— |
| 20 | —COOCH$_2$C$_6$H$_{11}$ | —CN | H | O | —CH$_2$CH(OOC$_6$H$_{11}$)CH$_2$— |
| 21 | —COOC$_6$H$_{10}$-4-C(CH$_3$)$_3$ | —CN | H | O | OOCC$_6$H$_4$-4-(CH$_2$)$_6$H<br>\|<br>—CH$_2$CHCH$_2$— |
| 22 | —COOCH$_2$C$_6$H$_4$-4-O(CH$_2$)$_{10}$H | —CN | H | O | OOCNHC$_6$H$_4$-4-CH$_3$<br>\|<br>—CH$_2$CHCH$_2$— |
| 23 | —COO(CH$_2$)$_9$H | —CN | H | O | —CH$_2$CH(OOCCH$_2$CN)CH$_2$— |
| 24 | —COO(CH$_2$)$_{19}$H | —CN | H | O | —CH$_2$CH(OOCCH$_2$OH)CH$_2$— |
| 25 | —COOCH$_2$CH(OH)CH$_2$OH | —CN | H | O | —CH$_2$C(CH$_2$OH)$_2$CH$_2$— |
| 26 | —COOCH$_2$C$_6$H$_4$-4-CH$_2$OH | —CN | H | O | —CH$_2$C(CH$_3$)$_2$CH$_2$— |
| 27 | —COOCH$_2$C$_6$H$_4$-4-C(CH$_3$)$_2$CH$_2$C(CH$_3$)$_3$ | —CN | H | O | —CH$_2$CH(CN)CH$_2$— |

TABLE I-continued

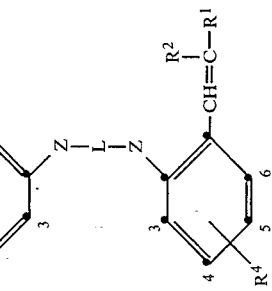

| Example | R¹ | R² | R⁴ | Z | L |
|---|---|---|---|---|---|
| 28 | —COOC₆H₄-4-O(CH₂)₁₀H | —CN | H | O | COO(CH₂)₄H<br>\|<br>—CH₂CHCH₂— |
| 29 | —COOCH₂CH₂NHCO(CH₂)₆H | —CN | H | O | O(CH₂)₆H<br>\|<br>—CH₂CHCH₂— |
| 30 | —COO(CH₂)₄CN | —CN | H | O | OC₆H₄-4-C(CH₃)₂CH₂C(CH₃)₃<br>\|<br>—CH₂—CHCH₂— |
| 31 | —COOCH₂CH₂S(CH₂)₁₀H | —CN | H | O | —CH₂CH(SO₂C₆H₁₁)CH₂— |
| 32 | —COOCH₂CH(OOCOC₂H₅)CH₂OOCOC₂H₅ | —CN | H | O | —CH₂CH[SO₂(CH₂)₁₈H]CH₂— |
| 33 | —SO₂(CH₂)₄H | —CN | H | O | —CH₂CH=CHCH₂— |
| 34 | —SO₂CH₂CH(CH₃)₂ | —CN | H | O | —CH₂C≡CCH₂— |
| 35 | —SO₂CH₂CH(C₂H₅)(CH₂)₄H | —CN | H | O | —CH₂CH(OH)CH(OH)CH₂— |
| 36 | —SO₂(CH₂)₁₈H | —CN | H | O | —CH₂CH₂OCOOCH₂CH₂— |
| 37 | —SO₂C₆H₁₀-3-CH₃ | —CN | H | O | —CH₂CH₂OOC(CH₂)₄COOCH₂CH₂— |
| 38 | —SO₂CH₂C₆H₄-4-(CH₂)₆H | —CN | H | O | —CH₂C₆H₁₀-4-CH₂— |
| 39 | —SO₂CH₂C₆H₄-4-(CH₂)₁₂H | —CN | H | O | —CH₂CH₂NHCO(CH₂)₄CONHCH₂CH₂— |
| 40 | —SO₂C₆H₄-4-O(CH₂)₉H | —CN | H | O | —CH₂CH₂OOC(CH₂)₄O— |
| 41 | —SO₂(CH₂)₄OH | —CN | H | O | —CH₂CH₂OC(CH₂)₄O— |
| 42 | —SO₂(CH₂)₆H | —CN | H | O | —CH₂CH₂SC₆H₄-2-S—CH₂CH₂— |
| 43 | —CONH(CH₂)₆OH | —CN | H | O | SO₂C₆H₄-3-CH₃<br>\|<br>—CH₂CHCH₂— |
| 44 | —CONH(CH₂)₆OOCC₆H₁₁ | —CN | H | O | —CH₂CH(OC₆H₁₁)CH₂— |
| 45 | —CONH(CH₂CH₂O)₂H | —CN | H | O | —CH₂CH[O(CH₂)₁₀H]CH₂— |
| 46 | —CONHCH₂CH₂OC₆H₅ | —CN | H | O | —CH₂CHClCH₂— |
| 47 | —CONHC₆H₄-4-O(CH₂)₄H | —CN | H | O | —CH₂CH₂OC₆H₄-4-OCH₂CH₂— |
| 48 | —CONH(CH₂)₁₀H | —CN | H | O | —CH₂CH[SC₆H₄-4-(CH₂)₄H]CH₂— |

TABLE I-continued

![structure with two substituted phenyl groups connected by N-L-N, each with CH=C(R²)(R¹) and R⁴ substituent]

| Example | R¹ | R² | R⁴ | Z | L |
|---|---|---|---|---|---|
| 49 | —CON(CH₃)(CH₂)₁₈H | —CN | H | O | —CH₂CH(CH₃)CH₂— |
| 50 | —CON[(CH₂CH₂O)₂H]₂ | —CN | H | O | —CH₂CH(C₆H₅)CH₂— |
| 51 | —CON(C₆H₅)CH₂CH₂OC₂H₅ | —CN | H | O | —CH₂CH(CONH₂)CH₂— |
| 52 | —CON(C₆H₁₁)(CH₂)₁₉H | —CN | H | O | —CH₂CH[COO(CH₂)₄H]CH₂— |
| 53 | —CONH(CH₃)C₆H₁₀-4(CH₂)₄H | —CN | H | O | —(CH₂)₆— |
| 54 | —CONCH₂CH₂OCH₂CH₂ (cyclic) | —CN | H | O | [triazine ring with OC₆H₄-2-CH=CCONCH₂CH₂OCH₂CH₂ and CN substituents] |
| 55 | —CONCH₂CH₂N[(CH₂)₆H]CH₂CH₂ (cyclic) | —CN | H | O | [OC₆H₄-2-CH=CCONCH₂CH₂NCH₂CH₂ with CN and (CH₂)₆H substituents] |
| 56 | —CON(CH₂)₅ (cyclic) | —CN | H | O | —CH₂CHOC₆H₄-2-CH₂— and —CH₂CH[O(CH₂)₁₃H]CH₂— |
| 57 | —C₆H₄-4-CN | —CN | H | O | —CH₂CH₂— |
| 58 | —C₆H₄-4-COO(CH₂)₄H | —CN | H | O | —CH₂CH₂— |
| 59 | —C=N-o-C₆H₄O (cyclic) | —CN | H | O | —(CH₂)₄— |
| 60 | —C=N-o-C₆H₃(5-COOCH₃)O (cyclic) | —CN | H | O | —CH₂C₆H₄-4-CH₂— |

TABLE I-continued

[Structure: Ar–N=L=N–Ar where each aryl group is a phenyl ring with positions 3,4,5,6 labeled, bearing R⁴ substituent and a CH=C(R²)–R¹ group]

| Example | R¹ | R² | R⁴ | Z | L |
|---|---|---|---|---|---|
| 61 | —C≡N-o-C₆H₄S— | —CN | H | O | —(CH₂)₃— |
| 62 | —C≡N-o-C₆H₄NH— | —CN | H | O | —CH₂C₁₀H₆-4-CH₂— |
| 63 | —C≡NN=C(CH₃)O— | —CN | H | O | —CH₂NC(O)N(CH₂—)CH₂CH₂— |
| 64 | —C≡NN=C(C₆H₅)S— | —CN | H | O | —CH₂CH₂OOCC₆H₃-3-COOCH₂CH₂— |
| 65 | —C≡CHCH=CHO— | —CN | H | O | —CH₂C(O)CH₂— |
| 66 | —C≡CHNHN=C— | —CN | H | O | —C=NC(OCH₃)=NC=N— |
| 67 | —CH=CHSCH=CH— | —CN | H | O | —C=NC=NC=N—CH=C(CN)—CH=CHSCH=CH— |
| 68 | —C≡N-o-C₆H₄C(O)NH— | —CN | H | O | —CH₂CH₂— |

TABLE I-continued

| Example | R¹ | R² | R⁴ | Z | L |
|---|---|---|---|---|---|
| 69 | —C=CH—N=CH—CH (cyclic) | —CN | H | O | —CH₂CH₂— |
| 70 | —C=CH-o-C₆H₄—N=CH (cyclic) | —CN | H | O | —CH₂CH₂— |
| 71 | —COOC₂H₅ | —CN | H | S | —(CH₂)₄— |
| 72 | —COOCH₃ | —CN | H | S | —CH₂CH₂— |
| 73 | —COO(CH₂)₁₀H | —CN | H | S | —CH₂CH₂— |
| 74 | —CN | —CN | H | O | —CH₂CH₂— |
| 75 | —COC(CH₃)₃ | —CN | H | O | —CH₂CH₂— |
| 76 | —COOC₆H₅ | —CN | H | O | —CH₂CH₂— |
| 77 | —COC=CHCH=CHS (cyclic) | —CN | H | O | —CH₂CH₂— |
| 78 | —C=NCH=CHS (cyclic) | —CN | H | O | —CH₂CH₂— |
| 79 | —COC₆H₄-4-CN | —CN | H | O | —CH₂CH₂— |
| 80 | —COOC₂H₅ | —COOC₂H₅ | H | O | —CH₂CH₂— |
| 81 | —C=N-o-C₆H₃(5-COOC₂H₅)O (cyclic) | —COOC₂H₅ | H | O | —CH₂CH₂— |
| 82 | —SO₂C₆H₅ | —COOC₂H₅ | H | O | —CH₂CH₂— |

TABLE I-continued

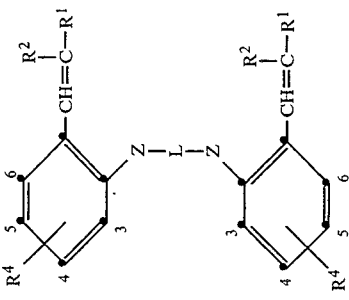

| Example | R¹ | R² | R⁴ | Z | L |
|---|---|---|---|---|---|
| 83 | —C=N-o-C₆H₃(5-COOC₂H₅)S | —COOCH₃ | H | O | —CH₂CH₂— |
| 84 | —COC₆H₄-4-OCH₃ | —COOC₂H₅ | H | O | —CH₂CH₂— |
| 85 | —COC₆H₅ | —COOC₂H₅ | H | O | —CH₂CH₂— |
| 86 | —COO(CH₂)₈H | —COO(CH₂)₈H | H | O | —CH₂CH₂— |
| 87 | —COOCH₂CH₂OH | —COOCH₂CH₂OH | H | O | —CH₂CH₂— |
| 88 | —C₆H₄-4-COOCH₃ | —COOCH₃ | H | O | —CH₂CH₂— |
| 89 | —COOCH₃ | —CN | 4-OCH₃ | O | —CH₂CH₂— |
| 90 | —COOC₂H₅ | —CN | 5-C₆H₅ | O | —CH₂CH₂— |
| 91 | —COO(CH₂)₄H | —CN | 3,5-di-CH₃ | O | —CH₂CH₂— |
| 92 | —COOCH₂CH₂OCH₃ | —CN | 5-Cl | O | —CH₂CH(OH)CH₂— |
| 93 | —CN | —CN | 4-CH₃ | O | —CH₂CH(OH)CH₂— |
| 94 | —COOCH₃ | —CN | 4-OCH₃ | O | —(CH₂)₄— |
| 95 | —COOH | —CN | H | O | —CH₂CH₂OCH₂CH₂— |
| 96 | —COOCH₃ | —CN | 5-C₆H₁₁ | O | —CH₂CH₂— |
| 97 | —C=NCH=CHCH=N | —CN | H | O | —CH₂CH₂— |
| 98 | —C=N-o-C₆H₃-6-[(CH₂)₄H]S | —CN | H | O | —CH₂CH₂— |
| 99 | —C=N-o-C₆H₃-6-[(CH₂)₄H]S | —CN | H | O | —CH₂CH₂— |

TABLE II

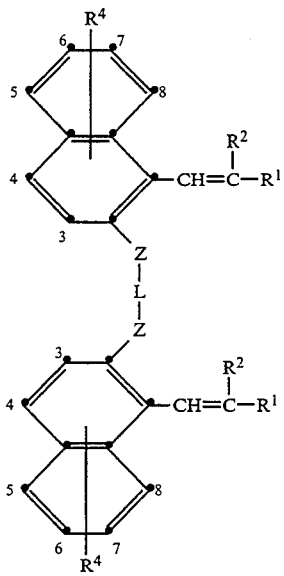

| Example | R¹ | R² | R⁴ | Z | L |
|---|---|---|---|---|---|
| 100 | —COOCH₃ | —CN | H | O | —CH₂CH₂— |
| 101 | —COOC₂H₅ | —CN | H | O | —(CH₂)₄— |
| 102 | —COO(CH₂)₄H | —CN | H | O | —(CH₂)₆— |
| 103 | —COO(CH₂)₈H | —CN | H | O | —CH₂CH₂OCH₂CH₂— |
| 104 | —COO(CH₂)₁₈H | —CN | H | O | —CH₂CH(OH)CH₂— |
| 105 | —COOCH₂CH(C₂H₅)(CH₂)₄H | —CN | H | O | —CH₂CH₂— |
| 106 | —COOC₂H₅ | —CN | H | S | —CH₂CH₂— |
| 107 | —CN | —CN | H | O | —CH₂C₆H₄-4-CH₂— |
| 108 | —SO₂CH₃ | —CN | H | O | —CH₂CH₂OC₆H₄-4-OCH₂CH₂— |
| 109 | —SO₂C₆H₅ | —CN | H | O | —CH₂CH(OOCCH₃)CH₂— |
| 110 | —SO₂C₆H₁₁ | —CN | H | O | —CH₂CH=CHCH₂— |
| 111 | —CONH(CH₂)₄H | —CN | H | O | —CH₂C≡CCH₂— |
| 112 | —CON(CH₂CH₂OH)₂ | —CN | H | O | —CH₂CH₂SCH₂CH₂— |
| 113 | —CONHC₆H₅ | —CN | H | O | —CH₂CH[O(CH₂)₄H]CH₂— |
| 114 | —CONHC̄=N-o-C₆H₄S̄ | —CN | H | O | —CH₂CH₂SO₂CH₂CH₂— |
| 115 | —CONHC̄=NN=C(SC₂H₅)S̄ | —CN | H | O | —CH₂C₆H₁₀-4-CH₂— |
| 116 | —C₆H₄-4-COOCH₃ | —CN | H | O | —CH₂CH(OH)CH(OH)CH₂— |
| 117 | —C̄=N-o-C₆H₄Ō | —CN | H | O | —CH₂CH₂OCOOCH₂CH₂— |
| 118 | —C̄=N-o-C₆H₄S̄ | —CN | H | O | -1,4-C₆H₄— |
| 119 | —C̄=NN=C(C₆H₅)Ō | —CN | H | O | —CH₂C(CH₃)₂CH₂— |
| 120 | —C̄=NC(CH₃)=CHS̄ | —CN | 6-CH₃ | O | —CH₂CH₂— |
| 121 | —COC₆H₅ | —CN | 3-OCH₃ | O | —CH₂CH₂— |
| 122 | —COC(CH₃)₃ | —CN | 6-OCH₃ | O | —CH₂CH₂— |
| 123 | —CO(CH₂)₆H | —CN | 3,4-di-Cl | O | —CH₂CH₂— |
| 124 | —COOC₂H₅ | —COOC₂H₅ | 4-Cl | O | —CH₂CH₂— |
| 125 | —C̄=N-o-C₆H₃(5-COOC₂H₅)Ō | —COOC₂H₅ | 5-OCH₃ | O | —CH₂CH₂— |
| 126 | —C₆H₄-4-COOCH₃ | —COOCH₃ | 2,5-di-OCH₃ | O | —CH₂CH₂— |
| 127 | —COOH | —CN | H | O | —CH₂CH₂— |
| 128 | —COOCH₂CH=CH₂ | —CN | H | O | —CH₂CH₂— |

TABLE II-continued

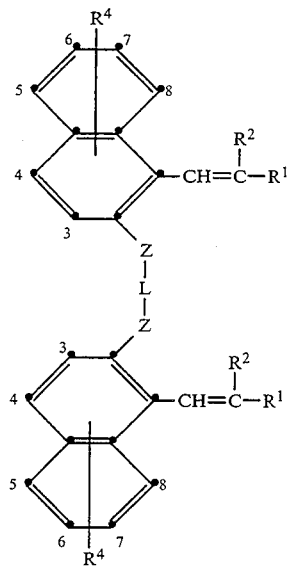

| Example | R¹ | R² | R⁴ | Z | L |
|---------|----|----|----|---|---|
| 129 | —COOC$_6$H$_{11}$ | —CN | H | O | —CH$_2$CH$_2$— |
| 130 | —COOCH$_2$CH$_2$OC$_6$H$_5$ | —CN | H | O | —CH$_2$CH$_2$— |

The sunscreen formulations provided by this invention include compositions comprising at least one of the poly-methine compounds of formula (I) dissolved, suspended or dispersed in a dermatologically-acceptable base. For example, the poly-methine compounds may be dissolved or dispersed in mineral oil, water-ethanol, hexylene glycol, isopropyl myristate, isopropyl palmitate, poly(alkylene glycols) such as poly(propylene glycol) having a molecular weight of about 400 to 1000 and various cosmetic oils such as almond, apricot kernel, avocado, castor, citrus seed, coconut cacao butter (also known as oil of theobroma), corn, cottonseed, egg, jojoba oil lanolin, linseed, mink, olive, palm, peach kernel, peanut, rapeseed, safflower, sesame, shark, soybean, turtle, whale and wheat germ.

Additional types of cosmetic oils or other usable vehicles include pharmaceutical grades of synthetic oils derived from natural fatty products (such as those available from Drew Chemical Corp. under the name Neobee M-5), acetylated monoglycerides (Myvacet), dimethyl phthalate, liquid paraffin, silicones, oleyl alcohols, stabilized castor oil, stabilized castor oil combined with either polyethylene glycol 400 dilaurate or triethanolamine oleate, liquid paraffin combined with stabilized castor oil, stearic acid, wool alcohol, cetyl alcohol, Polawax (a polyethylene ester of sorbitan), glycerin, sodium citrate, silicon fluid such as MS200 perfume oil, water, N,N-diethyltoluamide, glyceryl monostearate, Polychol 5 (an ethoxylated lanolin alcohol preparation), butylated hydroxytoluene, hydroxyethyl cellulose, and carboxymethyl cellulose, triethanolamines, light amber petrolatum, calcium stearate, kaolin, Croda liquid base, water-soluble vinyl polymers (such as available from B.F. Goodrich Chemical Co. under the name Carbopol 940), Arlacel, Tween, glycerol monostearate, carbowaxes, methocels, boric acid, ammonyxes, ethoxylated derivatives of lanolin and lanolin components (such as are available from American Cholesterol Products under the name Solulan 16), spermaceti, hexadecyl alcohol, surface active lanolin derivatives (such as are available from American Cholesterol Products, Inc. under the name Amerchol L-101), microcrystalline wax, beeswax, borax, lanogene, acetylated lanolin, polyoxyethylene oleate/laurate, polyethoxylated high molecular weight amides (such as Ethomid HT/15 from Armour Industrial Chemical Co.), polyoxyethylene ethers of higher aliphatic alcohols (such as those available from ICI under the name Brijs) and the like.

The oil solutions/dispersions may be combined with surface active agents commonly used in cosmetic preparations and emulsified with water to obtain either water in oil or, preferably, oil in water emulsions. The concentration of poly-methine compound in such sunscreen formulations typically will be in the range of about 0.1 to 20.0 weight percent and more commonly about 2.5 to 10.0 weight percent, based on the total weight of the sunscreen formulation.

Another embodiment of the sunscreen formulations according to our invention comprises a polyester having reacted therewith or copolymerized therein the residue of at least one of the poly-methine compounds of formula (I) wherein the poly-methine compound bears at least one and preferably two substituents that are reactive with one of the monomers from which the polyester is derived. Examples of the requisite reactive groups are set forth hereinabove.

The polyesters which may be used in the preparation of the polymeric sunscreen compositions include thermoplastic, crystalline or amorphous polyesters produced by conventional polymerization techniques using one or more diols and one or more dicarboxylic acids or ester-forming equivalents thereof. Typically, the polyesters have a number average molecular weight of about 3,000 to 50,000 and an inherent viscosity of about 0.1 to 0.6, measured at 25° C. using 0.5 g of polymer per 100 mL of a solvent consisting of 60 parts by weight phenol and 40 parts by weight tetrachloroethane.

The diol components of the described polyesters may be selected from ethylene glycol, propylene glycol, 1,3-propanediol, 1,4-butanediol, 2,2-dimethyl-1,3-propanediol, 1,6-hexanediol, 1,2-, 1,3- and 1,4-cyclohexanedimethanol, 1,2-, 1,3- and 1,4-cyclohexanediol, X,8-bis(hydroxymethyl)-tricyclo[5.5.1.0]-decane wherein X is 3, 4 or 5, and polydiols such as diethylene glycol, triethylene glycol, tetraethylene glycol, poly(ethylene glycol) having a molecular weight of about 200 to 10,000, dipropylene glycol, tripropyleneglycol, tetrapropylene glycol poly(propylene glycol having a molecular weight of about 500 to 4,000 and poly(1,4-butanediol), or poly(tetramethylene glycol), having a molecular weight of about 800 to 10,000. The cycloaliphatic diols may be employed as their cis or trans isomers or a mixture thereof.

The dicarboxylic acid residues of the polyesters may be derived from aliphatic, cycloaliphatic and aromatic dicarboxylic acids such as terephthalic acid, isophthalic acid, 1,2-, 1,3- and 1,4-cyclohexanedicarboxylic acid, succinic acid, glutaric acid, sebacic acid, 1,12-dodecanedioic acid, 2,6-napthalenedicarboxylic acid and the like. Either the dicarboxylic acid or ester-forming equivalents thereof such as anhydrides, acid chlorides or, especially, esters such as the dimethyl, diethyl, dipropyl and bis(2-hydroxyethyl) esters, may be used. The preferred polyesters comprise at least 50 mole percent terephthalic acid and/or 2,6-naphthalenedicarboxylic acid residues and at least 50 mole percent of diols selected from ethylene glycol, 1,4-butanediol, 1,6-hexanediol, 2,2-dimethyl-1,3-propanediol, 1,4-cyclohexanedimethanol or a mixture thereof. The polyester component of the polymeric sunscreen compositions most preferably comprises at least 90 mole percent terephthalic and/or 2,6-naphthalenedicarboxylic acid residues and at least 90 mole percent of residues of ethylene glycol, 1,4-butanediol, 1,6-hexanediol, 2,2-dimethyl-1,3-propanediol, 1,4-cyclohexanedimethanol or a mixture thereof.

The concentration of the residue of the polymethine compound of formula (I) in the polyester can be varied substantially depending, for example, on the amount of the polyester used in the sunscreen composition. Concentration of about 1.0 to about 50.0 weight percent, based on the weight of the polyester, may be used with a concentration of about 5.0 to 30.0 weight percent being preferred.

The polyester in which at least one of the compounds of formula (I) has been reacted or copolymerized may be used in the preparation of sunscreen compositions by dissolving or dispersing the polyester in a cosmetically-acceptable base. If the polyester is insoluble in the cosmetic base, dispersion and consequent particle size reduction can be accomplished by any of the methods practiced by those skilled in the art, including 3-roll milling using a cosmetic oil or base and surface active agents described hereinabove.

The polymer compositions provided in accordance with this invention comprise a condensation polymer, e.g., casting, extrusion or molding grade polyester or polycarbonate, (1) having physically admixed therein one or more of the poly-methine compounds of formula (I) or (2) having reacted therewith or copolymerized therein the residue of a least one of the compounds of formula (I). This embodiment of our invention can be used in the manufacture of film, sheet material, packaging material and other shaped articles for protecting various products from UV radiation. The casting or molding grade polyesters employed in this embodiment of our invention typically have an inherent viscosity of about 0.4 to 1.2 and are comprised of at least 50 mole percent terephthalic acid residues, 1,4-cyclohexanedicarboxylic acid residues, 2,6-naphthalenedicarboxylic acid residues or a mixture thereof and at least 50 mole percent of ethylene glycol residues, 1,4-butanediol residues, 1,4-cyclohexanedimethanol residues or a mixture thereof. Particularly preferred casting and molding grade polyesters are comprised of about 75 to 100 mole percent terephthalic acid residues and about 75 to 100 mole percent ethylene glycol residues.

The sheet material manufactured from the aforesaid polymer compositions may be used in safety glass and eyeware including spectacles and contact lenses to protect the human retina against harmful UV-A and UV-B radiation. The surface of such polyester sheet material may be coated with a UV light-cured hard coat for use in safety lens material and UV light-blocking sheeting.

Typical polycarbonates which may be used in the preparation of the polymer compositions are disclosed in Kirk-Othmer Encyclopedia of Chemical Technology, 3rd Ed., Volume 28, pages 479–494, the disclosure of which is incorporated herein by reference.

The most preferred casting, extrusion and molding grade polyesters which may be used in our novel polymeric compositions comprise poly(ethylene terephthalate) and poly(ethylene terephthalate) wherein up to 5 mole percent of the ethylene glycol residues have been replaced with residues derived from 1,4-cyclohexanedimethanol and wherein the polyesters have been sufficiently heat set and oriented by methods well known in the art to give a desired degree of crystallinity.

The concentration of the poly-methine compound or residue thereof in the casting, extrusion or molding grade condensation polymer can be varied substantially depending, for example, on the intended function of the UV-absorbing compound or residue thereof and/or the end use from which the polymer composition is designed. When the polymer composition is to be used in the fabrication of relatively thin-walled containers, e.g., about 10 to 30 mils thick, to screen UV light in the range of about 250 to 390 nm, the concentration of the poly-methine compound normally will be in the range of about 50 to 1500 ppm (parts by weight per million parts by weight polymer) with the range of 200 to 800 ppm being especially preferred. For polymer compositions destined for extrusion or casting into thin film, e.g., 1 to 10 mils thick, concentrations of about 1000 to 10,000 ppm of the poly-methine compound normally will be used. For example, for equivalent protection from UV light, a 7 mil-thick film will contain about 1600 ppm whereas a 2 mil-thick film will contain about 6000 ppm of at least one of the poly-methine compounds or a residue thereof.

The sunscreen formulations and polymeric compositions of our invention are further illustrated by the following examples.

EXAMPLE 131

A mixture of triethanolamine (0.50 g) in water (67.8 g) heated to 60° C. is added slowly to a rapidly-stirred, 70° C., brown solution of the following ingredients:

6.0 g Mineral oil (Exxon Primol 355);
7.0 g Isopropyl myristate;
3.0 g Glyceryl monostearate (Myverol 18-06);
3.0 g Propylene glycol;
3.0 g Stearic acid;
0.5 g Hexadecanol;

1.0 g Vitamin E (Eastman 6-40); and 8.0 g Compound of Example 4.

The mixture is stirred continuously while it cools to 40° C. and when the temperature is below 40° C. methyl paraben (0.05 g), propyl paraben (0.05 g) and fragrance (0.10 g, Coppertone-type) are added and the mixture is cooled to room temperature. When applied to the skin, the cream has an acceptable smooth texture.

EXAMPLE 132

The following materials are placed in a 500-mL three-necked, round-bottom flask:

97 g (0.5 mol) dimethyl terephthalate 62 g (1.0 mol) ethylene glycol 0.00192 g Ti from a n-butanol solution of acetyl-triisopropyl titanate 0.0053 g Mn from an ethylene glycol solution of manganese acetate 0.0216 g Sb from an ethylene glycol solution of antimony acetate 0.0072 g Co from an ethylene glycol solution of cobaltous acetate The flask is equipped with a nitrogen inlet, stirrer, vacuum outlet, and condensing flask. The flask and contents are heated at 200° C. in a Belmont metal bath for 60 minutes and at 210° C. for 75 minutes with a nitrogen sweep over the reaction mixture. Then 1.57 mL of an ethylene glycol slurry of a mixed phosphorus ester composition (Zonyl A) which contains 0.012 g phosphorus is added. The temperature of the bath is increased to 230° C. At 230° C. dimethyl 3,3'-[1,2-ethanediyl-bis(oxy)bis-2,1-phenylene]bis[2-cyano-2-propenoate] (0.096 g, 1000 ppm) prepared in Example 1 is added to the flask. Five minutes after this addition, a vacuum with a slow stream of nitrogen bleeding in the system is applied over a five-minute period until the pressure is reduced to 200 mm Hg. The flask and contents are heated at 230° C. under a pressure of 200 mm Hg for 25 minutes. The metal bath temperature is increased to 270° C. At 270° C. the pressure is reduced slowly to 100 mm Hg. The flask and contents are heated at 270° C. under a pressure of 100 mm Hg for 30 minutes. The metal bath temperature is increased to 285° C. and the pressure is reduced slowly to 4.5 mm Hg. The flask and contents are heated at 285° C. under pressure of 4.5 mm Hg for 25 minutes. Then the pressure is reduced to 0.25 mm Hg and polycondensation is continued for 40 minutes. The flask is removed from the metal bath and is allowed to cool in a nitrogen atmosphere while the polymer crystallizes. The resulting polymer has an inherent viscosity of 0.60 measured in a 60/40 ratio by weight of phenol/tetrachloroethane at a concentration of 0.5 g per 100 mL. An amorphous 15 mil thick film molded from this polymer exhibits a strong absorption peak with a maximum at 357 nm.

EXAMPLE 133

Four hundred grams of polyethylene terephthalate (I.V.=0.71) are dry blended with 0.32 g (800 ppm) of the poly-methine compound of Example 2. The blend is dried overnight (16 hours) in a vacuum oven at 110° C. After drying, the material is melt blended and extruded into 10 mil film on a C. W. Brabender ¾ inch extruder (25 to 1 L/D). A transmission spectrum of the 10 mil film obtained using a Perkin-Elmer Lambda 6 UV/Vis Spectrophotometer shows strong absorption of light in the 300–400 nanometer wavelength range.

EXAMPLE 134

The following materials are placed in a 500-mL three-necked, round-bottom flask:

43.5 g (0.224 mol) dimethyl terephthalate 37.1 g (0.412 mol) 1,4-butanediol 0.0072 g Ti from a n-butanol solution of acetyl-triisopropyl titanate 22.0 g (0.051 mol) compound of Example 1

The flask is equipped with a nitrogen inlet, stirrer, vacuum outlet, and condensing flask. The flask and contents are heated at 200° C. in a Belmont metal bath for about 2 hours and then the temperature is increased to and maintained at 220° C. for 2 hours with a nitrogen sweep over the reaction mixture. After increasing the temperature to 230° C. and with a stream of nitrogen bleeding into the system, vacuum is applied slowly at about 230° C. until the pressure is reduced to about 0.5 to 1.0 mm Hg and the temperature is held at approximately 230° C. for 10 hours. The vacuum is removed and methyl benzoate (100 mL) is added dropwise with stirring. Heating at 230° C. is continued for 10–15 minutes as the polymeric composition dissolves. The hot solution then is transferred to a 2-L beaker and stirring is continued as the composition cools. When the composition becomes very viscous, n-hexane (600 mL) is added to facilitate stirring. The crystalline polymer is collected by filtration, reslurried twice in n-hexane to remove the methyl benzoate and then dried in a vacuum oven under nitrogen. A yield of 68.3 g (94.0% of theory) of a pale tan solid is obtained. The poly(1,4-tetramethylene terephthalate) obtained contains approximately 30.3 weight percent of the residues of the compound of Example 1 copolymerized therein and has an inherent viscosity of 0.337 measured at 25° C. using 0.5 g polymer per 100 mL of a solvent consisting of 60 parts by weight phenol and 40 parts by weight tetrachloroethane.

EXAMPLE 135

The procedure described in Example 134 is duplicated except that the polycondensation step is carried out at 235° C. for about 1 hour. The resulting polyester composition containing the residue of the compound of Example 1 copolymerized therein has an inherent viscosity of 0.184 measured in a 60/40 ratio by weight phenol/tetrachloroethane mixture at a concentration of 0.5 g per 100 mL.

EXAMPLE 136

The following materials are placed in a 500-mL three-necked, round-bottom flask:

182.8 g (0.749 mol) dimethyl 2,6-naphthalene-dicarboxylate 108.0 g (1.2 mol) 1,4-butanediol 0.0225 g Ti from a n-butanol solution of acetyl-triisopropyl titanate 22.0 g (0.051 mol) compound of Example 1

The flask is equipped with a nitrogen inlet, stirrer, vacuum outlet, and condensing flask. The flask and contents are heated in a Belmont metal bath under a nitrogen sweep at 200° C. for 1.75 hours, at 220° C. for 1 hour and at 230°0 C. for 1 hour. The reaction mixture then is heated at 240° C. for about 30 minutes at a reduced pressure of 0.5 to 1.0 mm Hg with a nitrogen stream bleeding into the flask. The vacuum is removed and methyl benzoate (125 mL) is added dropwise and stirring is continued at about 240° C. for 5–10 minutes as the polymeric composition dissolves. The hot solution then is transferred to a 2-L beaker and stirring is continued as the solution cools. When the mixture becomes viscous, acetone (1 L) is added to facilitate stirring. The crystalline polyester composition then is collected by filtration, reslurried first in acetone (1 L) and then n-hexane (1 L) to remove the methyl benzoate and then dried in a vacuum oven under nitrogen. The polymer composition, consisting of poly(1,4-tetramethylene 2,6-naphthalenedicarboxylate) having copolymerized therein 9.75 weight percent of the residue of the compound of Example 1, is obtained in a yield of 207 g (91.6% of theory). The polymeric composition has an inherent viscosity of 0.135 measured in a 60/40 ratio by weight phenol/tetrachloroethane mixture at a concentration of 0.5 g per 100 mL.

The invention has been described in detail with particular reference to preferred embodiments thereof, but it will be understood that variations and modifications can be effected within the spirit and scope of the invention.

We claim:

1. A compound having the formula

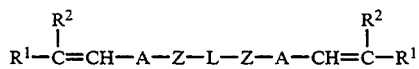

wherein
each $R^1$ is independently selected from; carboxy; $C_1$–$C_{24}$ alkoxycarbonyl, optionally substituted by a group selected from the group consisting of hydroxy, $C_1$–$C_{24}$ alkoxy, halogen, $C_1$–$C_{24}$ alkoxycarbonyl, cyano, $C_5$–$C_7$ cycloalkyl, $C_5$–$C_7$ cycloalkoxy, succinimido, and phthalimido; $C_5$–$C_7$ cycloalkoxycarbonyl or phenyloxycarbonyl or a naphthyloxycarbonyl radical; or a phenyl or naphthyl radical optionally substituted by a group selected from the group consisting of hydroxy, $C_1$–$C_{24}$ alkoxy, halogen, $C_1$–$C_{24}$ alkoxycarbonyl, cyano, $C_5$–$C_7$ cycloalkyl, $C_5$–$C_7$ cycloalkoxy, succinimido, and phthalimido;

each $R^2$ is independently selected from $C_1$–$C_{24}$ alkoxycarbonyl, optionally substituted by a group selected from the group consisting of hydroxy, $C_1$–$C_{24}$ alkoxy, halogen, $C_1$–$C_{24}$ alkoxycarbonyl, cyano, $C_5$–$C_7$ cycloalkyl, $C_5$–$C_7$ cycloalkoxy, succinimido, and phthalimido; $C_5$–$C_7$ cycloalkoxycarbonyl or a phenyloxycarbonyl or naphthyloxycarbonyl radical;

each A is independently selected from a 1,2-phenylene or 1,2-naphthylene radical;

each Z is independently selected from —O— or —S—; and

L is an organic linking group bonded by non-oxo carbon atoms to each Z atom, wherein said linking group is a $C_1$–$C_{12}$ alkylene, 2-hydroxy-1,3-propanediyl, 2-methyl- 1,3-propanediyl, oxy-bis-ethylene, oxy-bis-1,4-butanediyl, sulfonyl-bis-ethylene, thio-bis-ethylene, 1,2-, 1,3-, and 1,4-phenylene-bis-methylene, 1,2-, 1,3-, and 1,4-phenylene-bis-ethylene, 1,4-cyclohexylene-bis-methylene, 1,2-, 1,3-, and 1,4-phenylene-bis-(oxyethylene), methylsulfonylimino-bis-ethylene, phenylimino-bis-ethylene, acetylimino-bis-ethylene, and 1,2-, 1,3-, and 1,4-phenylene.

2. A compound according to claim 1 wherein each A is unsubstituted 1,2-phenylene.

* * * * *